(12) United States Patent
Sopori et al.

(10) Patent No.: US 8,780,343 B2
(45) Date of Patent: Jul. 15, 2014

(54) WAFER SCREENING DEVICE AND METHODS FOR WAFER SCREENING

(75) Inventors: Bhushan Sopori, Idledale, CO (US); Przemyslaw Rupnowski, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 13/146,111

(22) PCT Filed: Feb. 11, 2011

(86) PCT No.: PCT/US2011/024584
§ 371 (c)(1),
(2), (4) Date: Jul. 25, 2011

(87) PCT Pub. No.: WO2012/108882
PCT Pub. Date: Aug. 16, 2012

(65) Prior Publication Data
US 2013/0329221 A1 Dec. 12, 2013

Related U.S. Application Data (63) Continuation-in-part of application No. 11/722,981, filed as application No. PCT/US2006/029765 on Jul. 28, 2006, now Pat. No. 8,006,566, application No. 13/146,111, which is a continuation-in-part of application No. 12/919,433, filed as application No. PCT/US2009/036896 on Mar. 12, 2009.

(51) Int. Cl.
*G01N 21/00* (2006.01)

(52) U.S. Cl.
USPC .................................................. 356/237.5

(58) Field of Classification Search
CPC ...... G01N 21/9505; G01N 25/72; G01N 3/60

USPC ............................................ 356/237.1–237.5
See application file for complete search history.

(56) References Cited

U.S. PATENT DOCUMENTS

| | | | | |
|---|---|---|---|---|
| 3,917,414 A | * | 11/1975 | Geis et al. | 356/431 |
| 4,601,576 A | * | 7/1986 | Galbraith | 356/237.3 |
| 4,755,654 A | | 7/1988 | Crowley et al. | |
| 4,789,771 A | | 12/1988 | Robinson et al. | |
| 4,846,746 A | | 7/1989 | Prost | |
| 4,874,940 A | * | 10/1989 | McMeekin et al. | 250/223 B |
| 4,982,347 A | | 1/1991 | Rackerby et al. | |
| 5,239,357 A | * | 8/1993 | Hess | 356/237.1 |
| 5,304,509 A | | 4/1994 | Sopori | |
| 5,358,574 A | | 10/1994 | Sopori | |
| 5,387,557 A | * | 2/1995 | Takagi | 438/758 |
| 5,410,162 A | | 4/1995 | Tigelaar et al. | |
| 5,426,061 A | | 6/1995 | Sopori | |
| 5,429,985 A | | 7/1995 | Sopori | |
| 5,446,825 A | | 8/1995 | Moslehi et al. | |
| 5,452,396 A | | 9/1995 | Sopori | |
| 5,577,157 A | * | 11/1996 | Sopori | 392/416 |
| 5,614,020 A | | 3/1997 | Stevens et al. | |
| 5,619,462 A | | 4/1997 | McClure | |
| 5,639,520 A | | 6/1997 | Sopori | |
| 5,693,889 A | | 12/1997 | Nadolink | |
| 5,894,345 A | * | 4/1999 | Takamoto et al. | 356/237.1 |
| 5,897,331 A | | 4/1999 | Sopori | |
| 5,970,214 A | | 10/1999 | Gat | |
| 5,985,678 A | | 11/1999 | Kiyama | |
| 6,019,848 A | | 2/2000 | Frankel et al. | |
| 6,047,107 A | | 4/2000 | Roozeboom et al. | |
| 6,072,160 A | | 6/2000 | Bahl | |
| 6,103,552 A | | 8/2000 | Lin | |
| 6,201,261 B1 | | 3/2001 | Sopori | |
| 6,210,484 B1 | | 4/2001 | Hathaway | |
| 6,232,580 B1 | | 5/2001 | Sandhu | |
| 6,258,524 B1 | | 7/2001 | Hirabayashi | |
| 6,461,035 B2 | * | 10/2002 | Meinlschmidt et al. | 374/5 |
| 6,604,853 B2 | * | 8/2003 | Chao et al. | 374/57 |
| 6,734,117 B2 | | 5/2004 | Sogard | |
| 6,798,503 B2 | | 9/2004 | Hiramoto et al. | |
| 6,803,588 B2 | | 10/2004 | Kamieniecki | |
| 6,807,454 B2 | | 10/2004 | Wang et al. | |
| 6,816,251 B2 | | 11/2004 | Swan et al. | |
| 6,840,841 B2 | | 1/2005 | Hakomori | |
| 6,852,371 B2 | | 2/2005 | Sopori | |
| 6,861,268 B2 | | 3/2005 | Iwabuchi | |
| 7,113,272 B2 | * | 9/2006 | Bourely et al. | 356/237.1 |
| 7,238,912 B2 | | 7/2007 | Sopori | |

| | | | |
|---|---|---|---|
| 7,682,858 B2 | 3/2010 | Nagai et al. | |
| 7,773,211 B2 | 8/2010 | Borden | |
| 7,828,893 B2 | 11/2010 | Mueller et al. | |
| 8,006,566 B2* | 8/2011 | Sopori et al. | 73/800 |
| 8,268,733 B2* | 9/2012 | Tan et al. | 438/795 |
| 2002/0005400 A1 | 1/2002 | Gat | |
| 2002/0024659 A1* | 2/2002 | Tanaka | 356/237.2 |
| 2003/0068903 A1 | 4/2003 | Suzuki et al. | |
| 2005/0008218 A1 | 1/2005 | O'Dell et al. | |
| 2005/0066739 A1 | 3/2005 | Gotkis et al. | |
| 2005/0264798 A1 | 12/2005 | Nishiyama et al. | |
| 2005/0282299 A1 | 12/2005 | Kim et al. | |
| 2006/0037941 A1 | 2/2006 | Weng et al. | |
| 2006/0186354 A1 | 8/2006 | Kawase et al. | |
| 2007/0122936 A1* | 5/2007 | Park et al. | 438/77 |
| 2007/0122995 A1 | 5/2007 | Henley et al. | |
| 2007/0235769 A1* | 10/2007 | La Rosa et al. | 257/213 |
| 2008/0305615 A1 | 12/2008 | Ueno et al. | |
| 2010/0136715 A1 | 6/2010 | Sopori et al. | |
| 2011/0003485 A1* | 1/2011 | Sopori | 438/795 |
| 2011/0073869 A1 | 3/2011 | Buonassi et al. | |

FOREIGN PATENT DOCUMENTS

| | | | |
|---|---|---|---|
| JP | 60037116 | | 2/1985 |
| JP | 11351850 A2 | | 12/1999 |
| WO | PCT2006029765 | | 7/2006 |
| WO | PCT2008013547 A2 | | 1/2008 |
| WO | 2009148678 A2 | | 12/2009 |
| WO | WO 2009148678 A2 * | 12/2009 | H01L 21/324 |

OTHER PUBLICATIONS

Sopori, B., et al., A High Throughput, Noncontact System for Screening Silicon Wafers Predisposed to Breakage during Solar Cell Production, Abstract, 37th IEEE Photovoltaic Specialists Conf., Feb. 21, 2011.

International Search Report & Written Opinion, dated May 19, 2011, for International Application No. PCT/US11/24584.

Tsuo, Y.S., Pitts, J.R., High-flux solar furnace processing of silicon solar cells, Photovoltaic Energy Conversion, 1994, Conference Record of the Twenty Fourth; IEEE Photovoltaic Specialists Conference, 1994 IEEE First World Conference, vol. 2, Dec. 5-9, 1994 pp. 1307-1310.

Written Opinion and International Search Report dated Jan. 7, 2010 for International Application No. PCT/US09/36986.

Mier, Graphics Script Provides Quick Classification of GaAs Wafers, Reed Electronics, Apr. 1, 2000, Reed Elsevier Inc.

Higgs, Non-Destructive Optical Methods for Assessing Defects in Production of Si or SiGe Materials, The European Physical Journal, Feb. 10, 2004, 43-48, vol. 27.

International Search Report, dated Jul. 28, 2008, for International Application PCT/US06/29765.

\* cited by examiner

*Primary Examiner* — Gregory J Toatley
*Assistant Examiner* — Shawn Decenzo
(74) *Attorney, Agent, or Firm* — John C. Stolpa (57) ABSTRACT

Wafer breakage is a serious problem in the photovoltaic industry because a large fraction of wafers (between 5 and 10%) break during solar cell/module fabrication. The major cause of this excessive wafer breakage is that these wafers have residual microcracks—microcracks that were not completely etched. Additional propensity for breakage is caused by texture etching and incomplete edge grinding. To eliminate the cost of processing the wafers that break, it is best to remove them prior to cell fabrication. Some attempts have been made to develop optical techniques to detect microcracks. Unfortunately, it is very difficult to detect microcracks that are embedded within the roughness/texture of the wafers. Furthermore, even if such detection is successful, it is not straightforward to relate them to wafer breakage. We believe that the best way to isolate the wafers with fatal microcracks is to apply a stress to wafers—a stress that mimics the highest stress during cell/module processing. If a wafer survives this stress, it has a high probability of surviving without breakage during cell/module fabrication. Based on this, we have developed a high throughput, noncontact method for applying a predetermined stress to a wafer. The wafers are carried on a belt through a chamber that illuminates the wafer with an intense light of a predetermined intensity distribution that can be varied by changing the power to the light source. As the wafers move under the light source, each wafer undergoes a dynamic temperature profile that produces a preset elastic stress. If this stress exceeds the wafer strength, the wafer will break. The broken wafers are separated early, eliminating cost of processing into cell/module. We will describe details of the system and show comparison of breakage statistics with the breakage on a production line.

25 Claims, 9 Drawing Sheets

WAFER SCREENING DEVICE AND METHODS FOR WAFER SCREENING

CONTRACTUAL ORIGIN

The United States Government has rights in this invention under Contract No. DE-AC36-08GO28308 between the United States Department of Energy and the Alliance for Sustainable Energy, LLC, the manager and operator of the National Renewable Energy Laboratory.

BACKGROUND

Semiconductor wafers have the potential to fracture during processing. Semiconductor wafers include but are not limited to the silicon wafers commonly used as substrates for making photovoltaic devices. Wafer breakage during processing is costly, in part because of lost substrate materials, but more importantly because of the time and additional processing materials lost prior to wafer breakage.

One of the strategies for lowering the cost of silicon-based photovoltaic (PV) energy is to use thinner wafers for solar cell fabrication. This strategy reduces the wafer cost and increases solar cell efficiency, provided appropriate cell design and processing techniques are employed. Although the concept of reducing wafer thickness is quite straightforward, it is difficult to implement in manufacturing. The experience in the industry is that even with wafers of typical thickness, for example, wafers having a nominal thickness of about 250 µm, the breakage experienced during solar cell fabrication are quite high. The estimated fraction of wafers that break during cell fabrication and module encapsulation ranges between 5% and 10%. Additional reductions in wafer thickness have been found to further decrease the final product yield to unacceptable values because of breakage.

The yield loss due to wafer breakage has a considerable influence on the economies of producing solar cells. In particular, because the loss in revenue associated with wafer breakage increases as the cell fabrication process progresses, it is desirable to exclude those wafers that may break during cell processing before those wafers enter the fabrication lines. Identifying the sources of wafer breakage, understanding wafer breakage mechanisms, and developing methods of detecting and separating those wafers that are susceptible to breakage is of value, especially at early stages of solar cell fabrication.

Wafer breakage is not a major issue in other semiconductor industries which also uses silicon wafers. The computer semiconductor industry utilizes specific wafer preparation and pre-processing steps designed to minimize wafer breakage. These preventive measures add significant costs to a raw wafer however. In the photovoltaic industry it is not feasible to adopt these preventive measures due to the high cost associated with known semiconductor breakage prevention procedures. Thus, the excessive breakage of wafers experienced in the photovoltaic industry is exacerbated when compared to other semiconductor industries by relatively inadequate wafer preparation, inexpensive wafer handling techniques, and low-cost device processing methods, all of which are aimed at minimizing the cost of the resulting solar cell. In particular, relatively incomplete wafer preparation in the photovoltaic industry leaves defects such as microcracks at the surfaces and the edges of the wafers, which in turn lead to wafer breakage during cell fabrication as discussed herein.

Optical methods are sometimes used in the industry to detect flaws in wafers. For example, methods and apparatus are known for detecting a breakage producing flaw on the edge of a semiconductor wafer using an optical system, which illuminates the edge and measures the scattered radiation with optical detectors, microscopes, or other inspection devices.

Optical techniques however, are most well suited to detect and identify defects or flaws in semiconductor wafers which have polished surfaces. These techniques are difficult to use on photovoltaic wafers because these wafers typically have surfaces with relatively large roughness. The surface roughness "hides" such flaws and microcracks, making it difficult to recognize their presence by optical techniques. Furthermore, even if the detection of microcracks is accomplished, it is not straightforward to predict if the wafer will break during cell or module fabrication. Thus, it would be a significant contribution to the art to provide an effective non-optical method of rapidly screening wafers, which have defects that can result in the wafer breakage during device fabrication.

Commonly owned Patent Application PCT/US06/29765 entitled "Screening of Silicon Wafers Used in Photovoltaics" discloses a system and apparatus for the non-optical screening of wafers used in photovoltaics. The disclosure of the PCT/US06/29765 application is incorporated herein by reference for all matters disclosed therein. The methods and apparatus disclosed in the PCT/US06/29765 application are not however optimized for screening wafers at a rate suitable for the commercial production of photovoltaic devices.

The foregoing examples of the related art and limitations related therewith are intended to be illustrative and not exclusive. Other limitations of the related art will become apparent to those of skill in the art upon a reading of the specification and a study of the drawings.

SUMMARY OF THE EMBODIMENTS

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Multiple embodiments of a wafer screening device and a method of screening semiconductor wafers are disclosed. One embodiment comprises a wafer screening device having multiple diffuse reflecting walls defining an optical cavity. In addition, one or more light energy sources are placed in optical communication with the optical cavity such that the light energy sources may illuminate the optical cavity. An aperture defined by the optical cavity is also provided. In addition, a wafer transport mechanism is provided in optical communication with the aperture such that a wafer or a high volume of wafers may be transported through an illumination zone defined by the aperture.

The disclosed embodiments of a wafer screening device may also include one or more diffuse reflectors associated with the light energy sources. A diffuse reflector or diffuse reflecting wall as described herein has a surface which provides for a diffuse, non-specular reflection. For example, a diffuse reflecting surface may be fabricated from a high temperature ceramic having an appropriate surface texture.

The light energy sources of the wafer screening device may be located in a first portion of the optical cavity opposite the aperture. The aperture is therefore located in a second portion of the optical cavity. It should be noted that the terms upper and lower are sometimes used below to conveniently describe the first and second portions of the optical cavity. The disclosure encompasses embodiments where the aperture is above, below or beside the light energy sources.

In selected embodiments the multiple diffuse reflecting walls define a tapered optical cavity. The tapered optical cavity may taper in the shape of a funnel or pyramid with the light energy sources being located in the wider and typically, but not exclusively upper portion of the tapered cavity and the aperture being located in the narrower portion of the optical cavity. For example, the optical cavity may be defined by diffuse reflecting walls which taper toward the aperture at an angle of 10° to 40° with respect to a line between at least one of the light energy sources and the aperture.

The light energy sources may be implemented with any suitable illumination source. For example, the light energy sources could comprise three to five 1.6 kW tungsten-halogen lamps. In a multiple lamp configuration the lamps may be divided into multiple control zones and independently controlled with a computer or other techniques to achieve a desired flux output and flux profile in an illumination zone defined by the aperture.

A heat and stress profile may be introduced in a wafer transported through the illumination zone to stress test the wafers. An effective heat and stress profile may be introduced by providing an aperture which defines an opening having a length equal to or less than 15 mm and a width equal to or greater than 156 mm. As used herein the length is defined as the dimension parallel to the direction in which a wafer is transported through an illumination zone. The width is defined as being perpendicular to the direction of transport. Thus, a wafer being transported underneath the aperture through an illumination zone will be intensely illuminated and thereby heated in a narrow strip across the width of the wafer, which strip is moved as the wafer is transported through the illumination zone.

The screening device embodiments may be configured to provide for the transportation of equal to or greater than 1200 wafers per hour through the illumination zone to meet the demands of commercial solar cell production. The device may further comprise a heat extraction mechanism associated with the wafer transport mechanism to additionally stress wafers or provide for active cooling prior to additional processing steps.

Another embodiment disclosed herein is a method of screening wafers which comprises transporting a plurality of wafers through an illumination zone defined by the aperture of an optical cavity furnace as described above. The method thus includes illuminating the wafers with intense light energy and thereby heating portions of selected wafers to a selected temperature. A variable stress profile is thus introduced in the wafer since only a portion of the wafer is illuminated and the illuminated portion is moved as the wafer is transported through an illumination zone. Accordingly, the method comprises heating the wafers to create an unequal temperature distribution profile across the wafers surface. This unequal temperature distribution in turn creates a varying stress distribution within the wafer that can range from a local stress of greater than 0 MPa (Mega-Pascal) in a first portion of a wafer to a local stress of less than 100 MPa in another portion of the wafer. Thus, the apparatus and method may effectively be used to stress commercial quantities of semiconductor wafers prior to processing. Wafers that crack, break or otherwise fail initial stress testing can be removed from production lines prior to further processing steps.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Unless otherwise indicated, all numbers expressing quantities of ingredients, dimensions, reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise. A material may be described herein as being monocrystalline or multicrystalline. Monocrystalline material very specifically means an ingot, wafer or epilayer that is truly a single crystal, with no grain boundaries. Multicrystalline material or merely "Crystalline" is a more general term for a substantially crystalline material which does have grain boundaries. Crystalline shall be understood to mean substantially crystalline, and having a sufficiently well developed crystal structure that one skilled in the art would refer to the material as being crystalline. The terms crystalline, multicrystalline and monocrystalline do not mean absolutely defect free. Both types of material will have defects and or dislocations.

This disclosure provides a method and apparatus for the high throughput screening of semiconductor wafers potentially having a propensity for breakage, for example, due to the presence of microcracks and other defects. As described in detail below, the wafers are moved on a wafer transport system, which carries the wafers through the illumination zone of an optical cavity furnace, where stress is induced in each wafer. Wafers having fatal cracks or other defects may break as a result of this thermal stress, and thus may be eliminated from the fabrication line before further processing.

A semiconductor wafer experiences stresses from a variety of sources during device fabrication. These include but are not limited to: 1) wafer handling, such as mechanical handling during wafer transport; 2) structure of the device, such as asymmetry in the device configuration due to depositions of dielectric and/or metallic thin films that may cause wafer loading; 3) device processing, such as stresses that are induced during thermal treatments or rapid thermal processing.

A semiconductor wafer breaks if it experiences a tensile stress exceeding a critical stress. The intrinsic critical stress for most solid materials is quite high. A good mechanical/thermal design of a wafer, wafer transport, and fabrication process sequence strives to limit the wafer stresses to well below the critical stress values. The semiconductor industry uses design criteria for wafer preparation/handling and processing to achieve these goals. Initial industry studies have been carried out to evaluate stress produced by various thermal profiles in conventional furnaces. These studies determined that two parameters, wafer size and wafer thickness, are useful when considering potential stressors. Thus, the semiconductor industry uses standardized wafer thicknesses for various wafer sizes.

Studies on metals and glasses determined that, even for a suitably selected wafer of appropriate size and thickness, stress levels close to intrinsic values could be safely reached only for "well-prepared" wafers. Other wafers fracture at stress levels well below the intrinsic critical stress values. This reduction in the wafer strength was related to the surface and edge characteristics of the wafer.

The surface characteristics that may affect wafer breakage include at least shape, roughness, and surface damage. The shape of a semiconductor wafer is typically planar for other reasons. For example, based on device-processing considerations, the wafer surface must be planar and (in some cases) polished. Polishing also helps in mitigating wafer breakage. It has long been known that microcracks strongly control the mechanical strength of various commercial glasses. Crack-like defects have large local stresses that add to the externally developed stresses. Under uniaxial tensile loading of a material containing microcracks, the cracks begin to grow, which causes failure at stresses much below the theoretical strength. Microcracks often exist in semiconductor wafers, particularly those used to fabricate photovoltaic devices. Microcracks are typically generated in wafer-cutting processes such as sawing. In the semiconductor industry, cutting or sawing operations are followed by damage removal and polishing. The wafers may be chemically etched to remove the damaged layer at the surface, typically 10-20 µm in thickness, and then polished on one side.

Edge characteristics (such as shape of the edges and the technique of edge preparation) may also have significant effect on the breakage. Edge shaping typically uses a grinding process to "round off" the edges to minimize wafer breakage. Damage at the wafer edges (like surface damage) may also exist at the edges as a result of incomplete etching or edge preparation. Like surface damage, the residual edge damage may have a profound effect on the wafer strength. In some cases, the edge damage may be more harmful than the surface damage.

Because Si solar cell processing is (in many ways) similar to microelectronic device fabrication, the Si-photovoltaic industry had initially attempted to adopt many rules observed in the semiconductor industry. Wafer preparation and processing techniques were quite similar. However, with increased production and higher demands for solar cell cost reduction, the parallelism has significantly diminished. The need for cost reduction has led to an evolution of the technologies wherein the wafers are more fragile and the breakage rates are very significant. Although the exact causation for increased breakage observed in the photovoltaic industries is not known, it may be related to some of the procedures that are used in the photovoltaic industry (as summarized below).

Solar cell fabrication requires many process steps to convert an ingot of silicon into wafers and then process them into solar cells. Some of the process steps are similar to those used in the semiconductor industry. Typically, these steps include sawing, etching, formation of an N/P junction, and deposition of metallic and/or dielectric layers (some patterned and others in a blanket form). Although many process steps are performed at lower temperatures (<400° C.), some of these processes (such as phosphorus diffusion and Al alloying) are performed at elevated temperatures in which the temperature of the wafer itself may be non uniform.

Solar cell fabrication steps may be mechanically demanding on the strength of the wafer. Whereas the semiconductor industry takes adequate precautions that maintain the critical stress to near intrinsic values (to minimize wafer breakage), the photovoltaic industry cannot expend the resources necessary to suitably prepare wafers to reach the intrinsic critical stress level. The critical stresses for photovoltaic wafers are thus considerably smaller; the measured value of critical stress depends on the history of the wafer.

The major fabrication processes or attributes of materials used in the photovoltaic industry that are believed to contribute to high breakage are thus: 1) high throughput which demands high wafer transfer rates and faster processing times; 2) thin wafers; and 3) inadequate wafer preparation. The photovoltaic industry uses wafers that are much thinner than dictated by the semiconductor industry design rules. One reason is that thinner wafers are less expensive. The other reason is that a thinner solar cell may have higher efficiency (because the volume recombination is lower). Use of thinner wafers in the photovoltaic industry is also justified based on the number of process steps needed to fabricate a solar cell being a small fraction of the number of steps in microelectronics. However, thinner wafers have a lower mechanical strength. A reduction in the mechanical strength may also be partly contributed by rough or textured surfaces (to enhance optical absorption). In order to minimize the solar cell cost, damage etching and texture etching are combined into one step. This process step must be properly controlled in order to minimize breakage. In this process, there are many variables. For example, the texture etching bath is difficult to control because the etch composition changes as the wafers are etched; some wafers may have incomplete damage removal; and texture etching is typically done on a surface structure developed by exposing (111) crystallographic planes. Because these are cleavage planes, the textured wafer is more prone to cleavage.

The preparation of solar cell wafers may change the mechanical strength of a wafer. For example, sawing is a process of material removal by fracture (in which small fragments of material are chipped away). Such a process produces damage that may propagate quite deep below the surface into the material. Another process step that alters the mechanical properties of the wafer is texture etching. Although texture etching removes the saw damage (making it less likely to break), it exposes cleavage planes of the wafer, making them more likely to break in handling. Thus, cell processing itself may influence the state of stress in the wafer, which may change the propensity of the wafer toward breakage.

One way to determine if a wafer will break in a given process sequence is to simulate the stresses/stress-distributions (or the most stringent distribution) that the wafer will experience during that process. A standard method to determine critical stress is to apply a local tensile stress to a wafer until it fractures. A well-known approach consists of three-point loading, wherein the applied stress is increased until the wafer breaks. In a typical application, three-point loading is applied on a local region. This approach is good for double-sided polished wafers free from surface defects. When defects are present, the measured critical stress may depend on whether the measurement region contains surface defects.

In the photovoltaic industry, mechanical means of applying stress to the whole wafer is not convenient, for example, wafers may not have the same thickness or the wafers may not be uniform in thickness. Applying stress mechanically requires an elaborate means of both holding the wafer and a means of applying the stress. In particular, it is difficult to control the mechanical stress if the wafer is warped or does not have uniform thickness. Additionally, application of mechanical stress involves contact with surfaces that can cause contamination.

A method for testing the propensity of a wafer to break in typical solar cell processing that overcomes the difficulties of applying mechanical stress is described herein. This technique is a noncontact method. The basic principle of the described approach is to apply suitable stresses to a wafer with a predetermined configuration representative of solar cell processing/handling conditions. If the wafer breaks during this testing, the wafer is automatically pulled out of the processing line to save further processing costs. Another benefit of this method is to select wafers for further analyses that may identify reasons for wafer breakage.

The method of the current disclosure creates a stress distribution in the wafer by producing a thermal profile in the wafer through an optical excitation. The process consists of heating a wafer in a non-uniform manner to generate predetermined stresses.

Figure 1:
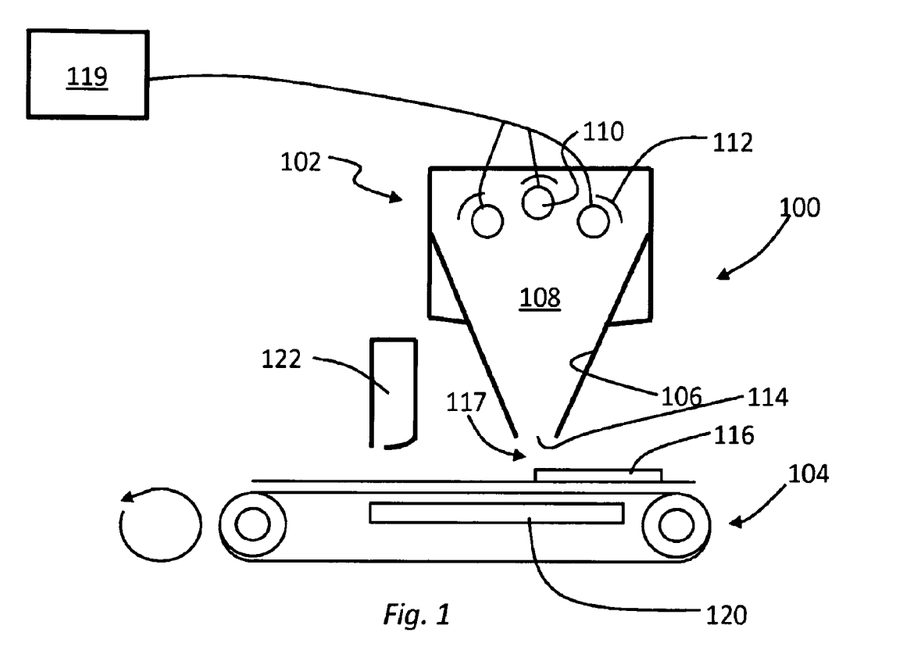
FIG. 1 is a schematic diagram of a wafer screening device.

As shown in FIG. 1 a wafer screening device 100 generally includes an optical cavity furnace 102 and wafer transport system 104 operatively associated with the optical cavity furnace 102. As also shown in FIG. 1 and shown with more specificity in FIG. 2, the optical cavity furnace 102 includes multiple reflecting walls 106 defining an optical cavity 108. As used herein, an optical cavity 108 is defined as an illuminated space from which optical energy may be applied to a wafer, typically through an aperture after reflection from or between multiple reflective surfaces or by direct radiation.

Accordingly, the device 100 and optical cavity furnace 102 will include one or more light energy sources 110 in optical communication with the optical cavity 102. The light energy sources 110 will typically be associated with reflectors 112 within the optical cavity 108. As described in detail below the reflectors 112 and the optical cavity walls 106 may be fabricated from any suitable material. A suitable material will be reflective and able to withstand the elevated temperatures present within the optical cavity furnace 102. For example, the optical cavity furnace walls 106 and reflectors 112 may be fabricated from a high temperature ceramic including but not limited to Zircar or other zironia, alumina or similar high-temperature ceramic material. These high-temperature ceramics offer a significant advantage in energy saving because unlike metallic reflectors they do not need water cooling. Certain advantages of an optical cavity furnace fabricated from high temperature ceramic materials are detailed in commonly owned Patent Application PCT/US09/36896 entitled "Optical Cavity Furnace for Semiconductor Wafer Processing. The disclosure of the PCT/US09/36896 application is incorporated herein by reference for all matters disclosed therein.

Certain unexpected advantages are observed when the reflecting surfaces of the optical cavity walls 106 and reflectors 112 have a diffusely reflective surface. One skilled in the art of fabricating an optical cavity furnace would typically choose to fabricate these elements with specular reflecting surfaces to most efficiently focus and concentrate optical energy at an operative location, for example, at an aperture 114. However, it has been determined that fabricating the furnace walls 106 and reflectors 112 with diffuse reflecting surfaces, although potentially less efficient than specular reflecting surfaces, facilitates more precise temperature control and thus facilitates enhanced overall system operation. A diffuse reflecting surface on the optical cavity furnace walls 106 or reflectors 112 may be provided by fabricating these elements with components having an appropriate level of surface roughness or other surface texture. In selected embodiments, the diffuse reflecting walls 106 are thermally insulated with insulation 118 (FIG. 2) and thus require no supplemental cooling, for example, no supplemental water cooling. Therefore, the primary energy transfer from the optical cavity 108 is to an illumination zone and then to an appropriate wafer only. In addition, the efficient coupling of light energy to a solar cell wafer that has very low reflectance due to roughness or texture reduces the overall energy requirements of the device 100.

Figure 2:
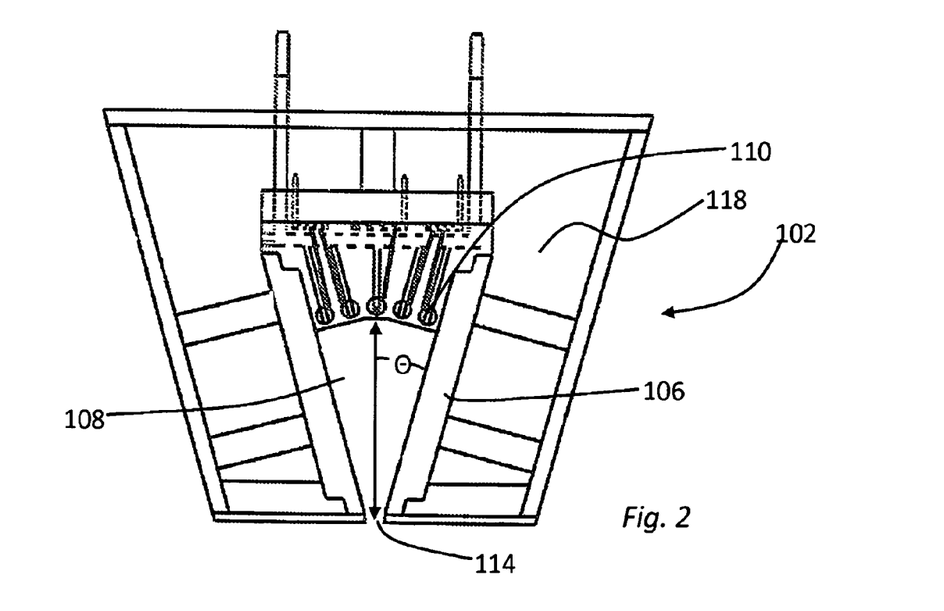
FIG. 2 is a front elevation cross-sectional view of the optical cavity furnace portion of a wafer screening device.

As shown on FIG. 1 and FIG. 2 the optical cavity furnace 102 will also include at least one aperture 114 defined by the optical cavity 108. Generally, the aperture will be located opposite the optical cavity 108 from the light energy sources 110 and reflectors 112. Thus, in use, light energy exits the optical cavity 108 in a controlled manner and will, as shown in FIG. 1, and described in detail below illuminate a portion of the surface of a wafer 116 as the wafer is transported through an illumination zone 117 and past the aperture 114. An aperture 114 may have any appropriate dimensions. For example, an aperture may have a width greater than the width of a wafer and a length substantially less than the length of a wafer. More specifically, an aperture may have a width of greater than 156 mm and a length of less than 15 mm. As used herein the width dimension is defined as being transverse the direction of travel provided by the wafer transport system 104. As described in detail below, the slot like configuration of an aperture 114 provides for the creation of a specific heat and stress profile within a selected wafer as the wafer is transported beneath the aperture. A single device 100 may have multiple apertures exiting a suitably sized optical cavity furnace 102 providing for the simultaneous screening of multiple parallel assembly lines of wafers.

The device and methods described herein are made more efficient because of the use of an optical cavity furnace 102 to couple light energy to a wafer surface. The efficiency of the overall system can be further enhanced by fabricating an optical cavity furnace 102 such that light energy generated by the light energy sources 110 is effectively channeled to the one or more apertures 114. As shown in FIGS. 1 and 2, effective optical coupling may be enhanced if the diffuse reflecting walls 106 define a tapered optical cavity 108. A tapered optical cavity is defined herein as an optical cavity having a cross sectional area at a first portion, for example an upper portion in FIGS. 1 and 2, in the vicinity of the optical energy sources 110, which is greater than a cross sectional area at another, second portion of the optical cavity near the aperture(s). As illustrated in FIG. 2, a tapered optical cavity may be fabricated by having the diffuse reflecting walls 106 positioned to define a slope toward the aperture at an angle Θ of about 10° to 40° with respect to a line between one or more of the light energy sources 110 and an aperture 114. As described above, certain advantages may be realized if the reflecting walls are fabricated from a material which provides for a diffuse reflection. In addition the light energy sources are operatively associated with diffuse reflectors 112. The combination of diffuse reflecting walls 106 defining a tapered optical cavity, diffuse reflectors and appropriately selected optical energy sources provide for the efficient coupling of light energy at the aperture. In addition, a bottom reflector 120 may be used to further enhance system efficiency.

As noted above, the aperture 114 may be an opening which is approximately equal to or somewhat greater than the width of a wafer but which defines an opening substantially less than the length of a wafer. This aperture configuration is advantageous for creating a dynamic temperature gradient within a wafer and thereby inducing stress in the wafer. Thus, elastic stress in the wafer is caused by creating a non-linear and dynamic temperature profile within the wafer. In use, a wafer moves linearly through an illumination zone with respect to an aperture. Since the aperture has a relatively narrow length, heat is applied across the wafer in a narrow band. Accordingly, the temperature profile of a given wafer changes as the wafer moves with respect to the aperture. In addition, both the optical flux intensity and its distribution within the aperture can be changed by having individual or grouped control of electrical excitation of the light sources. Control of individual lamps or groups of lamps may be automated by powering the light energy sources through a computerized control system 119.

To achieve a desired maximum temperature at any given point in time in a high temperature region of a wafer, the power applied to the light energy sources 110 along with individual or group control of the light energy sources, the aperture shape and size, and the translation speed of the wafer with respect to the aperture may all be controlled. For any selected power level and for any selected wafer translation speed, the combined effect of these variables causes complex stress distribution. The method and device described herein may be used to heat the surface of a wafer with light energy to create a varying stress distribution within the wafer, to create a stress maximum that ranges between 0 MPa and 100 MPa. In alternative embodiments, it may be advantageous to achieve a maximum stress level of about 40 MPa or 50 MPa.

Thus, elastic stress is induced in a selected wafer by controlling the wafer temperature in a relatively narrow heating zone at the aperture. For example, appropriate elastic stress may be induced in a wafer by heating a narrow region across a wafer, corresponding to the aperture, to 400° C. with as sharp a ramp up and ramp down of the temperature in the balance of the wafer as is possible. Since the wafer is moving with respect to the slot-like aperture, the region of the wafer which is experiencing maximum heating will be moved across the surface of the wafer while the wafer is moving with respect to the aperture. The heat induced stress will result in the breakage of wafers which have microcracks or other defects which in turn could result in wafer breakage during actual device processing steps.

Sufficient heat may be generated in a system processing 1200 wafers per hour with a single aperture by employing less than 1500 W of optical power. To produce 1500 W of optical power, an optical power source consuming approximately 4 kW of electric power may be used. For example, the device 100 can be implemented with three 1.6 kW tungsten-halogen lamps as the light energy sources 110. Alternatively, the device 100 could be implemented with five or another suitable number of 1.6 kW or other suitably sized tungsten-halogen lamps. In any selected multiple lamp configuration, the lamps may be divided into multiple control zones and independently controlled by computer 119 or other appropriate techniques to achieve a desired flux output and flux profile in an illumination zone defined by the aperture.

Typical processing equipment for the solar photovoltaic industry is presently scaled for a throughput of 1,200 wafers per hour. It is anticipated that the throughput figure will increase to 2,000 wafers per hour in the near future. Accordingly, it is desirable that a wafer screening device such as described herein will also have a throughput of between 1,200 to 2,000 wafers per hour, or even greater. Thus, the screening system can be incorporated into the front end of a photovoltaic production line to seamlessly screen wafers having a propensity to break from the line prior to subsequent device processing steps. If the device 100 has a single aperture, a transport speed of about 51 mm/sec will result in a throughput of approximately 1200 wafers per hour.

To cost justify screening every wafer in the manner described, the equipment and operational costs must be relatively low. The energy required to produce the desired thermal stress levels in typical 156 mm×156 mm wafers moving at a rate commensurate with 1,200-2,000 wafers per hour would be very large if the wafers were screened using conventional heat sources much as described in published Patent Application PCT/US06/29765. Furthermore, the use of conventional heating sources would require the additional energy cost of active heat removal from each wafer as it exited the wafer screening machine to prevent excessive heat buildup within the screening facility.

Both of the above challenges are in part addressed by the use of a device 100 featuring an optical cavity furnace 102 combined with a wafer transport system 104. As described above, the profile of the light flux at an aperture may be tailored by means of the selection and computerized zonal control of the primary light sources 110 and by selecting the shape of the reflective surfaces including reflectors and optical cavity walls. The wafer transport conveyor belt may be located over a bottom reflector 120 to further enhance efficiency. Additional control of the dynamic temperature profile may be provided by active cooling of the wafer as it moves away from the aperture, for example, by means of a jet of cold air provided from a cold air supply 122.

Figure 3:
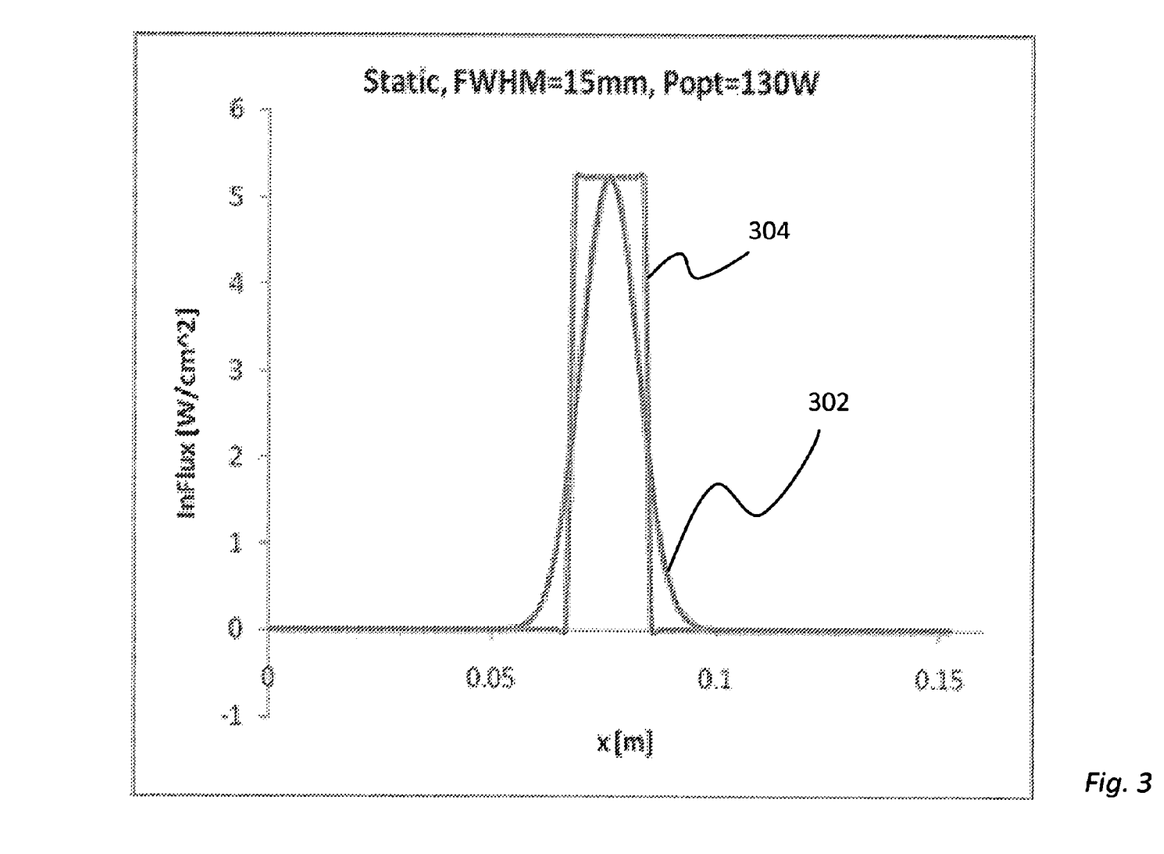
FIG. 3 is a graphic illustration of selected flux profiles.
Figure 4:
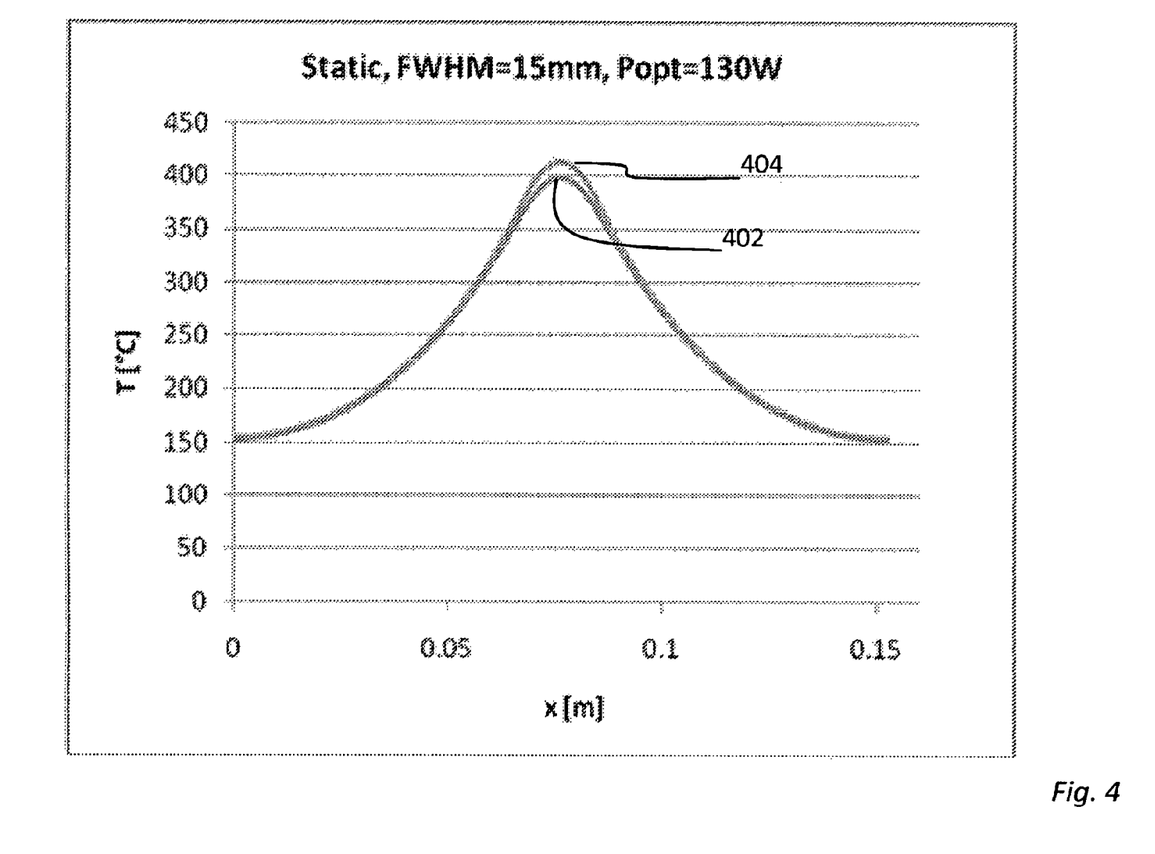
FIG. 4 is a graphic illustration of temperature profiles achieved by illuminating a wafer with the flux illustrated in FIG. 3, without moving the wafer.

The dynamic temperature profile and stress distribution achievable within a wafer with the device 100 and methods described herein may be predicted. For example, FIGS. 3 and 4 graphically illustrate a static (non-moving wafer) case where a 156 mm×156 mm wafer is illuminated with light energy having a Gaussian energy distribution 302 or flat top energy distribution 304 presented at an aperture having a length of 15 mm and centered over a 156 mm square wafer. As shown in FIG. 4, illumination for a short period of time with 130 W of optical energy in this configuration results in a peak temperature of about 400° C. across the center of the wafer tapering to a temperature of 150° C. at each edge. The temperature profile is similar whether the optical cavity is tuned to provide a Gaussian energy distribution (graph trace 402) or a constant energy distribution (graph trace 404) at the aperture.

Figure 5:
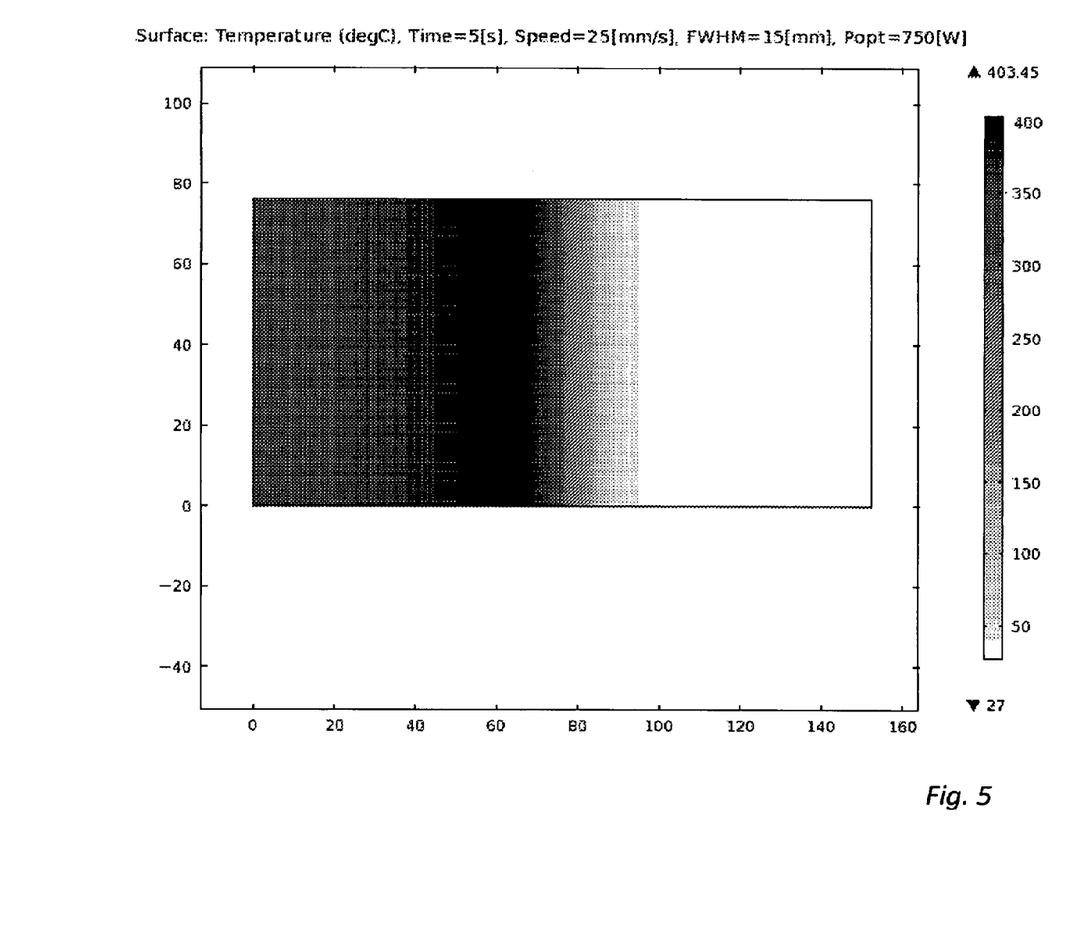
FIG. 5 is a two dimensional graphic illustration of the surface temperature profile predicted for a wafer moving through an illumination zone at the rate of 25 mm/sec.
Figure 6:
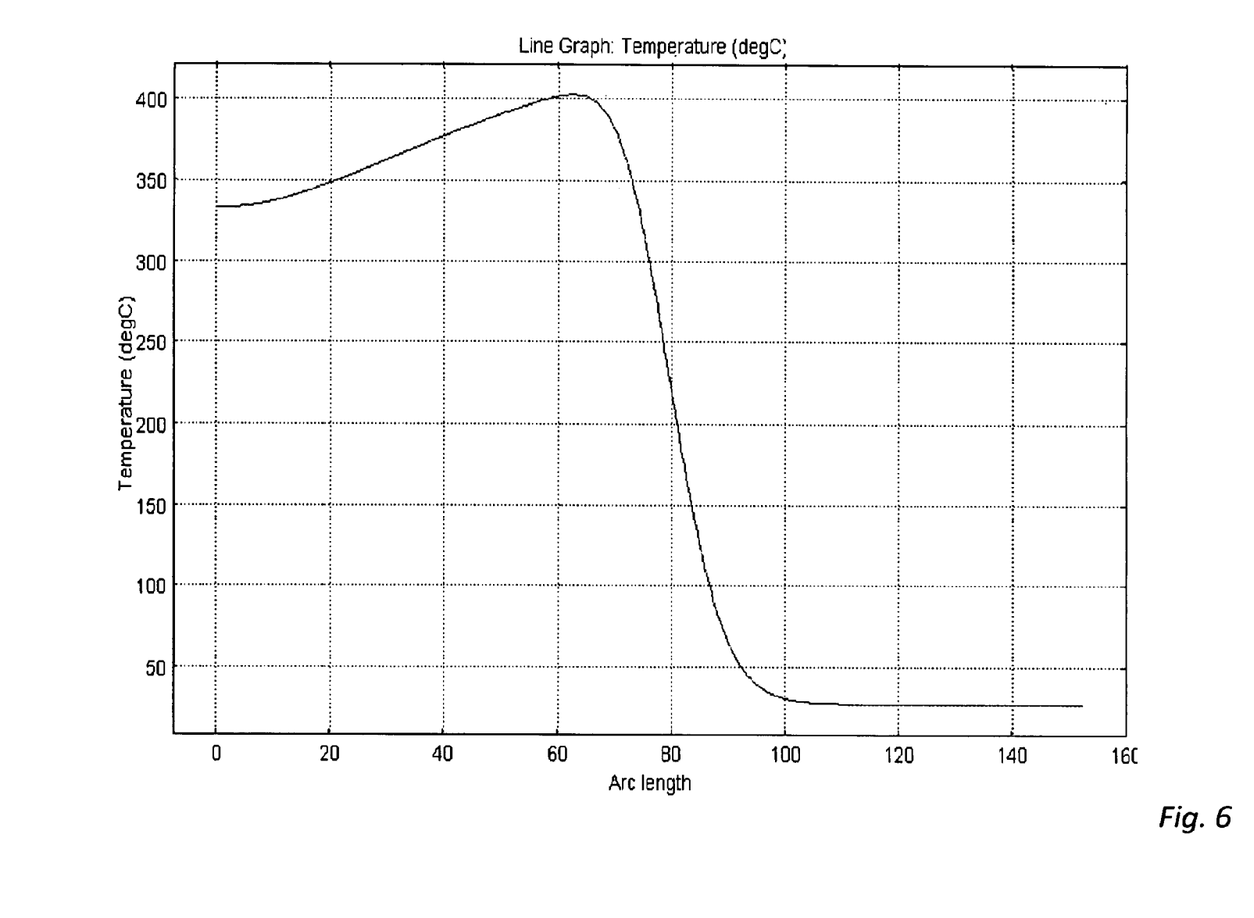
FIG. 6 is a line graph representation of the temperature profile shown in FIG. 5.
Figure 7:
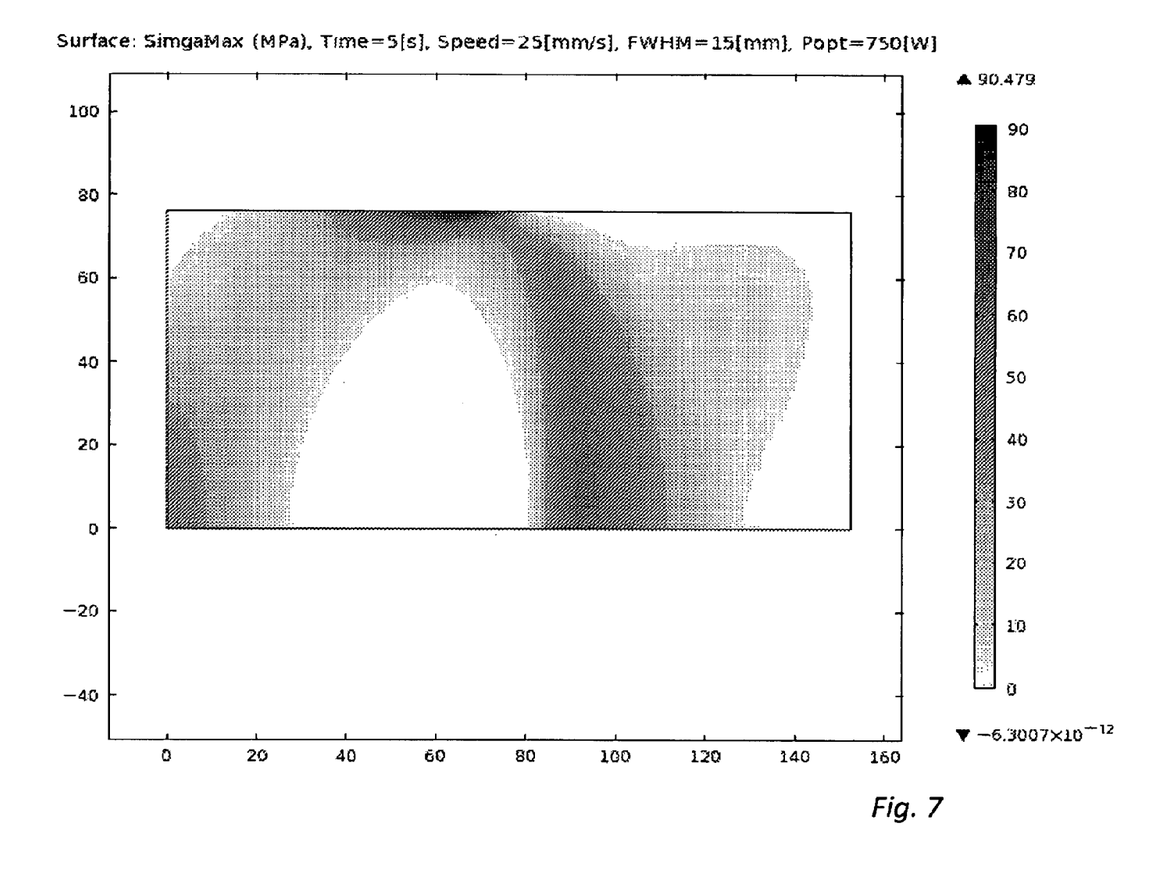
FIG. 7 is a two dimensional graph of the maximum surface stress induced in the wafer of FIG. 5-6.
Figure 8:
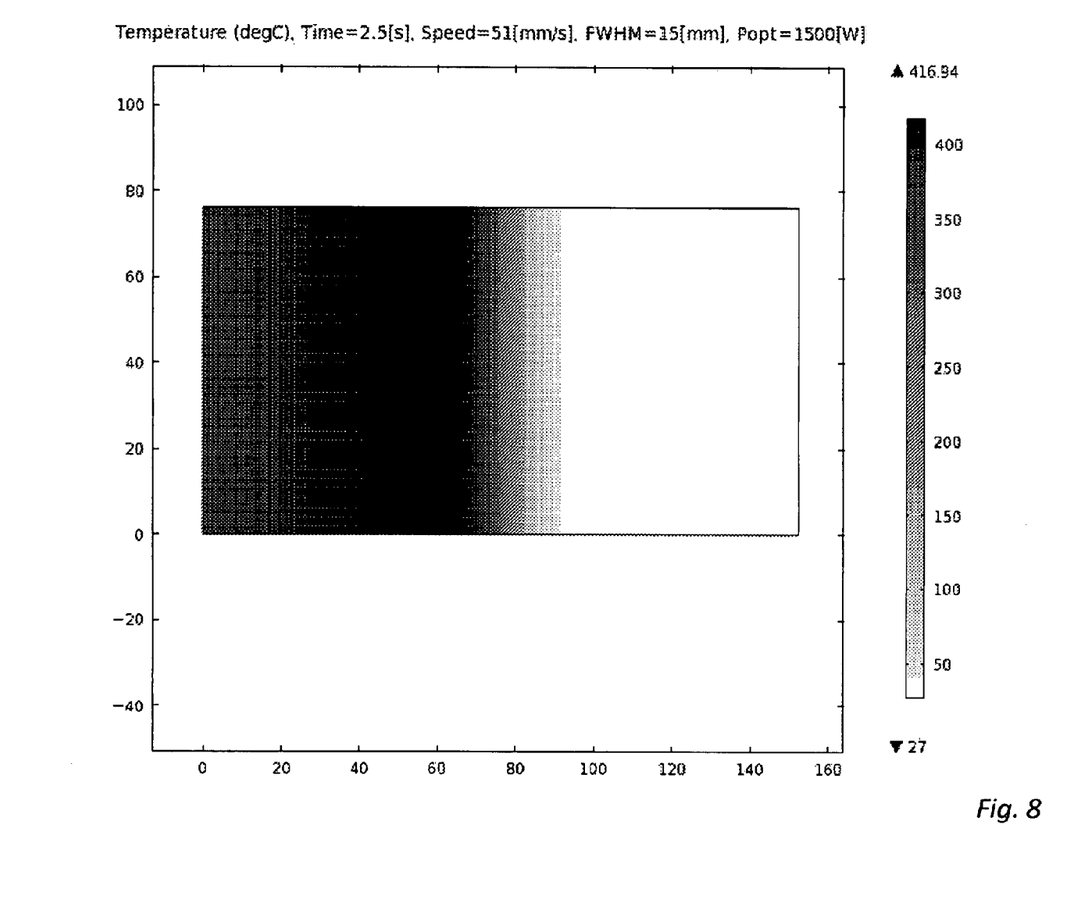
FIG. 8 is a two dimensional graphic illustration of the surface temperature profile predicted for a wafer moving through an illumination zone at the rate of 50 mm/sec.
Figure 9:
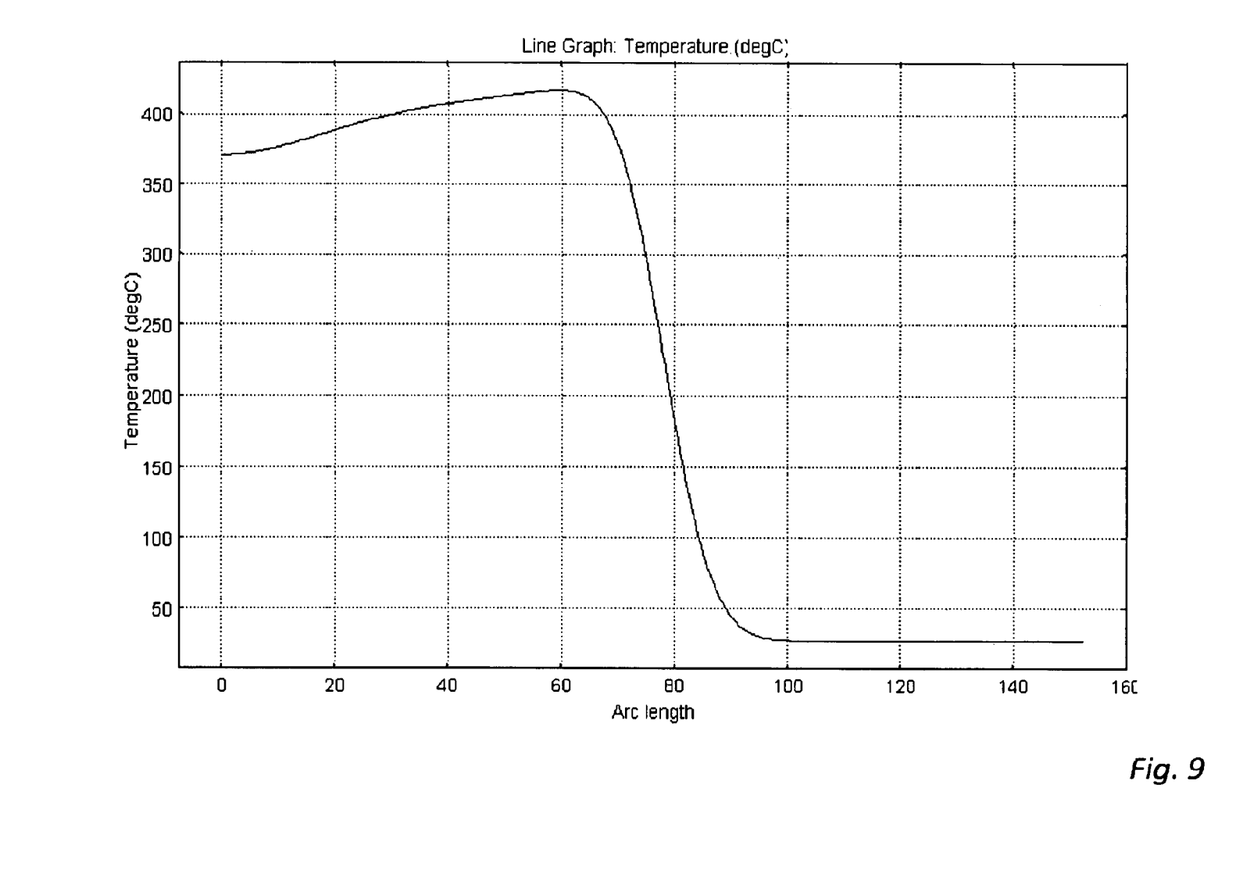
FIG. 9 is a line graph representation of the temperature profile shown in FIG. 8.
Figure 10:
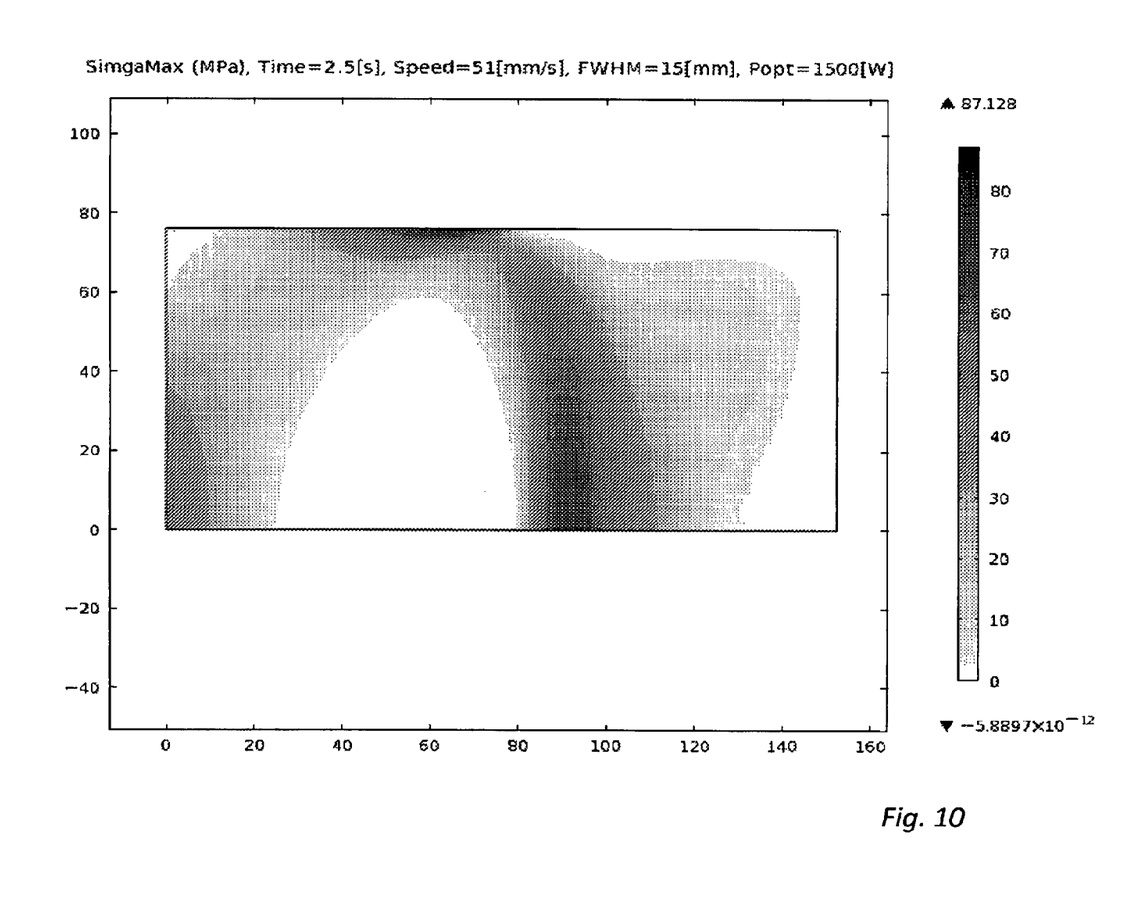
FIG. 10 is a two dimensional graph of the maximum surface stress induced in the wafer of FIG. 8-9.

FIGS. 5-7 graphically illustrate the predicted temperature and stress distributions in a wafer moving at the rate of 25 mm/sec. with respect to an aperture having full wafer width and a length of 15 mm. The temperature and stress models of FIGS. 5-7 are calculated based upon an assumed 750 W light source. FIGS. 5 and 6 illustrate the surface temperature over one side of the wafer, along the entire wafer length, at the point in time where the wafer is centered under the aperture. The wafer is moving from left to right. FIG. 7 illustrates the corresponding tensile stress distribution in the 156 mm×156 mm wafer at the same point in time as the temperature distribution of FIGS. 5 and 6 was calculated. Only the top half of the wafer (from 0 to 78 mm along the wafer width is shown, the bottom half from 0 to −78 mm is symmetrical. FIGS. 8-10 illustrate the same temperature and tensile stress information assuming that a 156 mm×156 mm is moving from left to right at the rate of 51 mm/sec. under a 1500 W light source.

The foregoing calculations demonstrate that an optical cavity furnace configured as described above can produce temperatures of up to 400 C in a wafer moving with respect to an aperture which provides for a wafer throughput of at least 1200 wafers per hour. Elastic stress of up to 100 MPa can be induced which is sufficiently high to break even those wafers that would survive normal fabrication steps.

The wafer transport system 104 may be provided in parallel tracks (not shown) to support wafers by their edges, accordingly, defective wafers which are induced to break may fall through the transport system 104 or be removed by visual inspection at a sorting station. Defective wafers may be removed for recycling. Wafers that are suitable for use in making electronic devices may be submitted to downstream processes, which may be any process to form electronic devices, such as photovoltaic cells, on the wafers. A programmable control unit 119 (FIG. 1) may be used to govern the delivery of optical energy by adjusting such parameters as the intensity of light from the optical source 110 and the speed of the transport system 104. These adjustments may be used to fine tune the screening process to minimize breakage losses that would otherwise occur in the downstream processes.

Thus, the device 100 is used to implement a method of screening a population of wafers that may have a high propensity to break during a solar cell fabrication process. Wafers having fatal microcracks may break as a result of this stress and will be eliminated from further processing—saving the processing costs of such wafers. The wafers that successfully pass this test have a high probability of survival through the process. Because the survival of a wafer (with microcracks) depends strongly on the methods used for wafer transport and processing conditions, changes in wafer handling/processing conditions may change the wafer yield. The system allows such changes to be accommodated simply by changing the optical excitation levels.

The present system and methods have many advantages which include the following: 1) it is a non contact method; 2) it represents real process conditions in which parameters maybe changed to reflect changes in process conditions; 3) it is relatively easy to control the stress configuration(s); 4) it may be combined and made part of solar cell processing (e.g., could be a drying process step); and 5) it may be easily incorporated into a wafer transport system.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure. Several embodiments have been particularly shown and described. It should be understood by those skilled in the art that changes in the form and details may be made to the various embodiments disclosed herein without departing from the spirit and scope of the disclosure and that the various embodiments disclosed herein are not intended to act as limitations on the scope of the claims. Thus, while a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A wafer screening device comprising:
   multiple diffuse reflecting walls defining an optical cavity;
   one or more light energy sources in optical communication with the optical cavity;
   an aperture defined by an opening from the optical cavity; and
   a wafer transport mechanism in optical communication with the aperture, wherein the wafer transport mechanism defines a direction of wafer travel and wherein the aperture comprises an aperture width transverse the direction of travel which is greater than the width of a wafer on the transport mechanism and wherein the aperture comprises an aperture length parallel to the direction of travel which is less than the length of a wafer on the transport mechanism.

2. The wafer screening device of claim 1 further comprising one or more diffuse reflectors associated with the one or more light energy sources.

3. The wafer screening device of claim 1 wherein the one or more light energy sources are located at a first portion of the optical cavity and the aperture is located at a second portion of the optical cavity, opposite the optical cavity from the one or more light sources.

4. The wafer screening device of claim 3 wherein the multiple diffuse reflecting walls extend from the first portion of the optical cavity to the second portion of the optical cavity and wherein the multiple diffuse reflecting walls define a tapered optical cavity having a cross sectional area at the first portion of the optical cavity which is greater than a cross sectional area at the second portion of the optical cavity.

5. The wafer screening device of claim 4 wherein the multiple diffuse reflecting walls defining the tapered optical cavity slope toward the aperture at an angle of 10° to 40° with respect to a line between at least one of the light energy sources and the aperture.

6. The wafer screening device of claim 1 wherein the multiple diffuse reflecting walls further comprise a high temperature ceramic material having a surface textured to provide for substantially non-specular reflection.

7. The wafer screening device of claim 1 wherein the aperture defines an opening having a length equal to or less than 15 mm and a width equal to or greater than 156 mm.

8. The wafer screening device of claim 1 further comprising a wafer transport mechanism providing for the transportation of equal to or greater than 1200 wafers per hour through an illumination zone defined by the aperture.

9. The wafer screening device of claim 8 further comprising a wafer transport mechanism comprising a conveyor belt providing for the movement of a series of wafers with respect to the aperture at a velocity equal to or greater than two inches per second.

10. The wafer screening device of claim 1 further comprising a heat extraction mechanism operatively associated with the wafer transport mechanism.

11. A method of screening a wafer comprising:
    providing a wafer screening device comprising multiple diffuse reflecting walls defining an optical cavity, one or more light energy sources in optical communication with the optical cavity, an aperture defined by an opening from the optical cavity and a wafer transport mechanism in optical communication with the aperture, wherein the wafer transport mechanism defines a direction of wafer travel and wherein the aperture comprises an aperture width transverse the direction of travel which is greater than the width of a wafer on the transport mechanism and wherein the aperture comprises an aperture length parallel to the direction of travel which is less than the length of the wafer on the transport mechanism;

associating a plurality of wafers with the wafer transport mechanism;

transporting the plurality of wafers through an illumination zone defined by the aperture; and illuminating the wafers with light energy thereby heating portions of selected wafers to a selected temperature.

12. The method of screening a wafer of claim 11 further comprising heating a surface of selected wafers with light energy to create an unequal temperature distribution profile across the wafer surface.

13. The method of screening a wafer of claim 12 further comprising heating the surface of selected wafers with light energy to create a varying stress distribution within the wafer that ranges from a local stress of greater than 0 MPa in a first portion of a wafer to a local stress of less than 100 MPa in another portion of a wafer.

14. The method of screening a wafer of claim 11 further comprising providing a wafer screening device wherein the multiple diffuse reflecting walls extend from a first portion of the optical cavity to a second portion of the optical cavity and wherein the multiple diffuse reflecting walls define a tapered optical cavity having a cross sectional area at the first portion of the optical cavity which is greater than a cross sectional area at the second portion of the optical cavity.

15. The method of screening a wafer of claim 14 wherein the multiple diffuse reflecting walls defining the tapered optical cavity slope toward the aperture at an angle of 10 to 40° with respect to a line between at least one of the light energy sources and the aperture.

16. The method of screening a wafer of claim 11 further comprising providing an optical cavity furnace wherein the aperture defines an opening having a length equal to or less than 15 mm and a width equal to or greater than 156 mm.

17. The method of screening a wafer of claim 11 further comprising transporting wafers through an illumination zone defined by the aperture at a rate of equal to or greater than 1200 wafers per hour.

18. The method of screening a wafer of claim 11 further comprising transporting wafers through an illumination zone defined by the aperture at a velocity of greater than two inches per second.

19. The method of screening a wafer of claim 11 further comprising extracting heat from the plurality of wafers after the wafers have been illuminated with optical energy.

20. A wafer screening device comprising:

means for illuminating an optical cavity;

means for diffusely reflecting light within the optical cavity;

an aperture defined by an opening from the optical cavity; and means for transporting a wafer in optical communication with the aperture, wherein the means for transporting a wafer defines a direction of wafer travel and wherein the aperture comprises an aperture width transverse the direction of travel which is greater than the width of a wafer on the means for transporting a wafer and wherein the aperture comprises an aperture length parallel to the direction of travel which is less than the length of a wafer on the means for transporting a wafer.

21. The wafer screening device of claim 20 wherein the means for diffusely reflecting light within the optical cavity comprises multiple diffuse reflecting walls extending from a first portion of the optical cavity to a second portion of the optical cavity and wherein the multiple diffuse reflecting walls define a tapered optical cavity having a cross sectional area at the first portion of the optical cavity which is greater than a cross sectional area at the second portion of the optical cavity.

22. The wafer screening device of claim 20 further comprising means for heating a surface of a wafer with light energy to create an unequal temperature distribution profile across the wafer surface.

23. The wafer screening device of claim 20 further comprising means for heating the surface of selected wafers with light energy to create a varying stress distribution within the wafer that ranges from a local stress of greater than 0 MPa in a first portion of a wafer to a local stress of less than 100 MPa in another portion of a wafer.

24. The wafer screening device of claim 20 wherein the means for transporting a wafer in optical communication with the aperture further comprising a wafer transport mechanism providing for the transportation of equal to or greater than 1200 wafers per hour through an illumination zone defined by the aperture.

25. The wafer screening device of claim 20 further comprising means for extracting heat from a wafer.

* * * * *